(12) United States Patent
Golz-Berner et al.

(10) Patent No.: US 7,329,636 B1
(45) Date of Patent: Feb. 12, 2008

(54) PERFUME WHOSE FRAGRANCE CAN BE CHANGED

(75) Inventors: Karin Golz-Berner, Jean-Charles Rey (MC); Leonhard Zastrow, Jean-Charles Rey (MC)

(73) Assignee: Coty B.V. (NL)

( * ) Notice: Subject to any disclaimer, the term of this patent is extended or adjusted under 35 U.S.C. 154(b) by 138 days.

(21) Appl. No.: 10/110,012

(22) PCT Filed: Oct. 6, 2000

(86) PCT No.: PCT/DE00/03598

§ 371 (c)(1),
(2), (4) Date: Apr. 8, 2002

(87) PCT Pub. No.: WO01/26612

PCT Pub. Date: Apr. 19, 2001

(30) Foreign Application Priority Data

Oct. 8, 1999 (DE) ................................ 199 49 418

(51) Int. Cl.
*A61Q 13/00* (2006.01)
(52) U.S. Cl. .............................................. 512/5; 512/1
(58) Field of Classification Search .................... 512/1, 512/5
See application file for complete search history.

(56) References Cited

U.S. PATENT DOCUMENTS 5,283,056 A * 2/1994 Chung et al. ................. 424/49
5,374,614 A * 12/1994 Behan et al. .................. 512/3
5,525,588 A * 6/1996 Michetti ........................ 512/4
6,403,109 B1 * 6/2002 Stora .......................... 424/401

FOREIGN PATENT DOCUMENTS

DE     695 00 050 T2    9/1996

OTHER PUBLICATIONS

Patent Abstracts of Japan No. 01-201261, published Aug. 14, 1989; inventor: T. Mitsuaki and M. Yishiaki.
Patent Abstracts of Japan No. XP-002163852.

* cited by examiner

*Primary Examiner*—Jill Warden
(74) *Attorney, Agent, or Firm*—Stephan Pendorf; Akerman Senterfitt

(57) ABSTRACT

The invention relates to a perfume which comprises at least two fragrance that can be selected by the user. According to the invention, the perfume contains two clear layers which are distinctly separated from one another with one layer being an aqueous, aqueous-alcoholic or isostearate derivative phase and the other layer being an oil phase. If the oil phase contains a silicone oil, the second layer is formed by a isostearate derivate. The aqueous phase contains at least one water-soluble fragrance and the oil phase contains at least one other oil-soluble fragrances. A mixed fragrance is created by shaking so that at least three different fragrances an be drawn from a perfume container.

17 Claims, No Drawings

PERFUME WHOSE FRAGRANCE CAN BE CHANGED

CROSS REFERENCE TO RELATED APPLICATION

This application is a national stage of PCT/DE00/03598 filed Oct. 6, 2000 and based upon DE 199 49 418.5 filed Oct. 8, 1999 under the International Convention.

BACKGROUND OF THE INVENTION

1. Field of the Invention

The invention relates to a perfume which comprises at least two fragrances that can be selected by the user.

2. Description of the Related Art

Perfumes with different fragrances have been used for thousands of years. The industrial production of essential oils and the synthesis of odorous substances improved both their availability and range of application. Perfumery focuses on the creation of new fragrances, which sometimes are composed of more than 100 individual components, and on fixing the base note in order to increase clinging and adhesion to the user's skin. Since perfumes have become a mass product, users wish to have different fragrances at their disposal and to be able to rapidly change the fragrance in some cases. Up to now, the only possibility for the user to do so consists in taking along several different perfumes and using them according to his/her wishes.

EP-A-692239 discloses a two-phase perfume which contains an aqueous-alcoholic phase containing a fragrance and another phase containing a volatile silicone oil. Further, U.S. Pat. No. 5,468,496 discloses a cosmetic product comprising two phases which rapidly separate from one another and in which the aqueous phase contains a demixing agent and at least one of the two phases contains a surface-active agent.

SUMMARY OF THE INVENTION

The object of the invention is to flexibly react to the users' wishes for change and to provide a perfume whose fragrance can be changed.

DETAILED DESCRIPTION OF THE INVENTION

According to the invention, the perfume consists of at least two clear layers which are distinctly separated from one another and of which the first layer is an oil phase and the second layer is an aqueous, aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25.

For the purposes of the present invention, the term "water-soluble fragrance" denotes a combined fragrance consisting of several fragrant components which is soluble in water or, as the case may be, in water/alcohol in the form of a clear solution.

For the purposes of the present invention, the term "oil-soluble fragrance" denotes a combined fragrance consisting of several fragrant components which is soluble in a cosmetic oil in the form of a clear solution.

For the purposes of the present invention, the term "perfume" denotes the overall composition consisting of at least two phases in which the total fragrance concentration can be in the range of 0.2 to 40% by weight. Therefore lower concentrations, in particular those below 10% by weight relative to the total weight of the composition, are also referred to as perfume herein.

Advantageously, the oil phase consists of a low-viscosity oil whose viscosity is between 100 and approximately 3,000 Pa·s with a viscosity of the oil similar to that of water being preferred. The viscosity is measured according to the Brookfield method using a No. 1 spindle at 25° C.

Advantageously, the oil is selected from the group consisting of fatty acid esters, silicone oils, vegetable oils and mixtures thereof. Preferred substances are Hexyl Laurate (Cetiol A), Cetyl Alcohol, Jojoba Oil, Silicone, Cetearyl Alcohol, Dicapryl Ether, Cetearyl Isononanoate, Palm Oil and Octyl Salicylate.

If the oil forming the first layer is a silicone oil, such as e.g. Dimethicone or Cyclomethicone, the second layer is formed by an isostearate derivative. The term "isostearate derivative" denotes cosmetically acceptable isostearates such as Propylene Glycol Diisostearate, Octyl Isostearate, Isostearyl Isostearate, Triisostearin, Isostearic Acid, Trimethylolpropane Triisostearate and Pentaerythrityl Tetraisostearate. Particularly preferred substances are Trimethylolpropane Triisostearate and Pentaerythrityl Tetraisostearate. The use of isostearate derivatives is advantageous as they are particularly compatible with fragrances, don't cause irritations of the skin and promote mixing of the phases.

Preferred phase combinations are an aqueous phase and a water-soluble fragrance combined with an oil phase comprising e.g. a fatty acid triglyceride of a medium-chain fatty acid and an oil-soluble fragrance; or an aqueous-alcoholic phase and e.g. a trivalent alcohol, such as Propylene Glycol, and a water-soluble fragrance combined with an oil phase comprising e.g. an isostearate derivative and an oil-soluble fragrance; or a silicone oil phase and an oil-soluble fragrance combined with a phase comprising an isostearate derivative, such as Trimethylolpropane Triisosterate, and a water-soluble fragrance.

The water-soluble fragrance is preferably selected from among Orange Oil, Rose Oil, Citronella Oil, Chamomile Oil, Lemon Oil, Lavender Oil and mixtures thereof and is used in the form of commercially available waters, e.g. Rose Water, Peppermint Water etc.

The oil-soluble fragrance is preferably selected from among Ambergris, Anethole $C_{10}H_{12}O$, Angelique Root Oil, Artemisia Oil, Basil Oil, Bay Oil, Benzaldehyde $C_7H_6O$, Bergamot Oil, Benzyl Acetate $C_9H_{10}O_2$, Camphor $C_{10}H_{16}O$, Calamus Oil, Carrot Oil, Coumarine $C_9H_6O_2$, Cypress Oil, Dihydromyrcenol $C_{10}H_{20}O$, Jasmine, Mimosa Muscone $C_{16}H_{30}O$, Narcissus, Sandalwood Oil, Vanilla Oil, Citron Oil and mixtures thereof. The invention is not limited to the aforementioned fragrances.

Preferably, the fragrances are selected and combined such that when mixing the two phases a mixed fragrance is created which is distinct from the two other fragrances and which is to be considered a third fragrance of the perfume according to the invention. The preferred perfume oils mentioned above are particularly suitable for this purpose.

The different fragrances contained in the at least two layers of the perfume enable the user to draw the desired perfume from the respective layer using simple means such as pipettes or dual pump heads arranged on a spray container. Further, it is possible to produce a third perfume by mixing the two phases and subsequently drawing the newly created fragrance from the temporary mixed phase. The selection of the individual fragrances contained in the aqueous phase and the oil phase will be decisive for the mixed fragrance, however, the latter can be easily predetermined by a person having the ordinary skill in the art. The aforesaid use is another object of the invention.

In order to slow down the separation of the aqueous phase and the oil phase after a mixing process and thus to extend the period of time during which the mixed fragrance can be drawn, appropriate oils, e.g. triglycerides, can be used in the oil phase in desired quantities.

After a mixing process has finished and the phases have re-established, the fragrances are present in their respective phases again and can be drawn separately, each with the carrier of the respective phase.

The aqueous phase can contain up to 30% by weight of a monovalent alcohol, in particular 1 to 10% by weight, in order that the fragrance dries more rapidly after it has been applied to a surface. Particularly suitable alcohols are $C_3$-$C_5$ alcohols such as e.g. Propanol or Isopropanol. The aqueous phase can also contain polyvalent alcohols, such as Propylene Glycol, in concentrations of 1 to 10% by weight, in both cases relative to the total weight of the composition.

The fragrance content of the oil phase can be in the range of 0.1 to 20% by weight relative to the weight of the respective phase, preferably 1 to 15% by weight and particularly 3 to 15% by weight. Another embodiment of the invention can contain fragrances in the range of 8 to 20% by weight relative to the weight of the phase.

The fragrance content of the aqueous phase can be in the range of 0.1 to 15% by weight, preferably 1 to 10% by weight.

In addition, both phases can contain auxiliary and active cosmetic substances such as e.g. UV filters. The presence of surface-active and/or demixing agents is ruled out.

Another embodiment of the invention consists in that more than two layers, e.g. three layers, containing different fragrances are provided. In this case, one layer consists of a pure aqueous phase, a second layer consists of an oil phase (e.g. a fatty acid triglyceride, a vegetable oil or an isostearate derivative) and a third layer consists of a special, light silicone oil phase, e.g. Cyclomethicone. The latter phase also forms a distinctly separate layer. The fragrance of each phase can be drawn separately and a fourth combined fragrance is created when all phases are shaken and the fragrance is drawn immediately after shaking. At this time, there exists an emulsion-like mixture for a short while, in which mixture the different fragrances form a mixed fragrance.

In the two-phase embodiment, the perfume can be contained in a spray container with dual pump head in which one suction tube of the pump head is immersed in the oil layer and in the aqueous layer, i.e. extends into the aqueous layer located below the oil layer, and the other suction tube is immersed in the oil layer only. In this way, it is made sure that when actuating the respective pump head the pump head raises the desired fragrance which is then sprayed at the spray nozzle.

In a similar way, the desired fragrance together with the carrier of the phase, e.g. water, can be drawn by means of a pipette, depending on the depth to which the latter is immersed.

In this way, it is also possible to offer different fragrances for partners (e.g. lady/gentleman) or fragrances for different times of the day in one container. Another advantage of the invention consists in that irritations of the skin, which are a problem for many users resulting from the high alcohol concentrations of up to 80% in usual perfumes, can be avoided.

By changing the ratio of the phase carriers, i.e. water to oil, to be near its extremes, different application forms can be provided. For example, a perfumed body spray can be manufactured if 65-70 parts by weight of the oil phase are used and the aqueous phase makes up the rest, and a hairspray can be manufactured if 65-70 parts by weight of the aqueous phase are used and the oil phase accounts for the rest.

In addition, the respective phase can also contain such sun filters which dissolve therein without affecting the clarity of the phase. Other additives for cosmetic applications can also be added if they do not affect the clarity of the solution or the stability of the phase.

The invention will hereinafter be explained in more detail by way of examples. All percentages are given in % by weight if not indicated otherwise.

EXAMPLE 1

| Aqueous phase | |
|---|---|
| Distilled Water | q.s. ad 100 |
| Rose Oil (water-soluble) | 10 |
| Oil phase | |
| Light Jojoba Oil | q.s. ad 100 |
| Cypress Oil (30%) and Jasmine Oil (70%) | 10 |

The phases are produced separately by mixing their respective ingredients. Subsequently, 60 parts by weight of the oil phase and 40 parts by weight of the aqueous phase are filled into a perfume container, such as a spray container, one after the other, which container is provided with a dual pump head and suction tubes which are connected to the latter and are different in length depending upon the layers formed. The respective phase can be sprayed by actuating one of the two pump heads individually. A mixed fragrance can be sprayed after thorough shaking of the container and actuating one of the two pump heads.

EXAMPLE 2

| Aqueous phase | |
|---|---|
| Distilled Water | 87 |
| Citronella Oil (water-soluble) | 10 |
| Benzophenone-4 | 3 |
| Oil phase | |
| Cetiol Hexyl Laurate | 82.5 |
| Angelique Root Oil | 10 |
| Octyl Salicylate | 7.5 |
| Silicone phase | |
| Cyclomethicone | 97 |
| Mimosa Muscone | 3 |

The three phases were prepared separately by mixing and subsequently filled into a perfume container in the following quantities: aqueous phase 36%, oil phase 30%, silicone phase 34%. The fragrances are drawn from the perfume container, from the desired layer or from the mixture produced by shaking which re-separates into the individual layers after a certain period of time, using a pipette.

EXAMPLE 3

| Trimethylolpropane Triisostearate | 47 |
| Rose Water | 3 |
| Propylene Glycol | 3 |
| Water | 44 |
| Citron Oil | 3 |

The ingredients are mixed as in Example 1 and the two phases are filled into a perfume container in a ratio of 50:50. A mixed fragrance is produced for a short time by mixing the two phases in the container.

EXAMPLE 4

| Cyclomethicone | 48 |
| Vanilla Oil | 2 |
| Trimethylolpropane Triisostearate | 48 |
| Rose Water | 2 |
| Processing is done as in Example 3. | |

What is claimed is:

1. A perfume whose fragrance can be changed, which comprises at least two clear layers which are distinctly separated from one another of which the first layer is an oil phase and the second layer is an aqueous, aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25, wherein a mixture of the water-soluble fragrance and the oil-soluble fragrance which is present after mixing the aqueous phase and the oil phase has a third fragrance other than the two first fragrances.

2. A perfume according to claim 1 wherein the oil phase contains low-viscosity oils whose viscosity is between 100 and 3,000 Pa·s.

3. A perfume according to claim 1 wherein the oils are selected from among fatty acid esters, silicone oils, vegetable oils and mixtures thereof.

4. A perfume according to claim 1 wherein the water-soluble fragrance is selected from among Orange Oil, Rose Oil, Citronella Oil, Chamomile Oil, Lemon Oil, Lavender Oil, each of them in a water-soluble form.

5. A perfume according to claim 1 wherein the oil-soluble fragrance is selected from among of Ambergris, Anethole $C_{10}H_{12}O$, Angelique Root Oil, Artemisia Oil, Basil Oil, Bay Oil, Benzaldehyde $C_7H_6O$, Bergamot Oil, Benzyl Acetate $C_9H_{10}O_2$, Camphor $C_{10}H_{16}O$, Calamus Oil, Carrot Oil, Coumarine $C_9H_6O_2$, Cypress Oil, Dihydromyrcenol $C_{10}H_{20}O$, Jasmine, Mimosa Muscone $C_{16}H_{30}O$, Narcissus, Sandalwood Oil and mixtures thereof.

6. A perfume according to claim 1 wherein the aqueous phase contains up to 30% by weight of a monovalent alcohol.

7. A perfume according to claim 6 wherein the monovalent alcohol is a $C_3$-$C_5$ alcohol.

8. A perfume according to claim 1 wherein the fragrance content of the respective phase is in the range of 0.1 to 20% by weight relative to the weight of the respective phase.

9. A perfume according to claim 1 wherein the perfume is present in a spray container with dual pump head in which one suction tube is immersed in the oil layer and the aqueous layer and the other suction tube is immersed in the oil layer only.

10. A perfume according to claim 1 wherein the first layer contains a fatty acid triglyceride and the second layer is an aqueous-alcoholic phase containing a monovalent $C_3$-$C_5$ alcohol.

11. A perfume whose fragrance can be changed, which comprises at least two clear layers which are distinctly separated from one another of which the first layer is an oil phase and the second layer is an aqueous aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25, wherein the oil phase contains low-viscosity oils whose viscosity is between 100 and 3,000 Pa·s.

12. A perfume whose fragrance can be changed, which comprises at least two clear layers which are distinctly separated from one another of which the first layer is an oil phase and the second layer is an aqueous, aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25, wherein the water-soluble fragrance is selected from among Orange Oil, Rose Oil, Citronella Oil, Chamomile Oil, Lemon Oil, Lavender Oil, each of them in a water-soluble form.

13. A perfume whose fragrance can be changed, which comprises at least two clear layers which are distinctly separated from one another of which the first layer is an oil phase and the second layer is an aqueous, aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25, wherein the aqueous phase contains up to 30% by weight of a monovalent alcohol.

14. A perfume according to claim 13 wherein the monovalent alcohol is a $C_3$-$C_5$ alcohol.

15. A perfume whose fragrance can be changed, which comprises at least two clear layers which are distinctly separated from one another of which the first layer is an oil phase and the second layer is an aqueous, aqueous-alcoholic or isostearate derivative phase wherein, if the oil phase contains a silicone oil, the second layer is a phase formed by an isostearate derivative and wherein the second layer comprises at least one water-soluble fragrance and the first layer comprises at least one oil-soluble fragrance other than the water-soluble fragrance and wherein the ratio of the aqueous or isostearate phase's weight to that of the oil phase is in the range of 25:75 to 75:25, wherein the first layer contains a fatty acid triglyceride and the second layer is an aqueous-alcoholic phase containing a monovalent $C_3$-$C_5$ alcohol.

16. A perfume whose fragrance can be changed, which comprises at least two clear layers which are distinctly second from one another of which the first layer is an isostearate derivative comprising phase and the second layer is an aqueous phase wherein, wherein the second layer comprises at least one water-soluble fragrance and the first layer comprises at least one fragrance soluble in the isostearate derivative comprising phase other than the water-soluble and wherein the ratio of the aqueous phase's weight to that of the isostearate derivative comprising phase is in the range of 25:75 to 75:25.

17. A perfume according to claim 16 wherein a mixture of the water-soluble fragrance and the fragrance soluble in the isostearate derivative comprising phase which is present after mixing the aqueous phase and the isostearate derivative comprising phase has a third fragrance other than the two first fragrances.

* * * * *